United States Patent [19]

Gray et al.

[11] 4,149,413

[45] Apr. 17, 1979

[54] OPTICALLY ACTIVE LIQUID CRYSTAL MIXTURES AND LIQUID CRYSTAL DEVICES CONTAINING THEM

[75] Inventors: George W. Gray, Cottingham; Damien G. McDonnell, Hull, both of England

[73] Assignee: The Secretary of State for Defence in Her Britannic Majesty's Government of the United Kingdom of Great Britain and Norther Ireland, London, England

[21] Appl. No.: 821,569

[22] Filed: Aug. 3, 1977

[30] Foreign Application Priority Data

Aug. 16, 1976 [GB] United Kingdom ............... 34063/76

[51] Int. Cl.$^2$ .......................... C09K 3/34; G02F 1/13; G01K 11/16
[52] U.S. Cl. ..................................... 73/356; 252/299; 252/408; 350/350; 350/351; 428/1; 23/230 LC
[58] Field of Search .................. 73/356; 252/299, 408; 350/160 LC, 350, 351; 428/1; 23/230 LC

[56] References Cited

U.S. PATENT DOCUMENTS

| | | | |
|---|---|---|---|
| 3,915,883 | 10/1975 | VanMeter et al. | 252/299 |
| 3,925,238 | 12/1975 | Gavrilovic | 252/299 |
| 3,947,375 | 3/1976 | Gray et al. | 252/299 |
| 3,951,846 | 4/1976 | Gavrilovic | 252/299 |
| 3,975,286 | 8/1976 | Oh | 252/299 |
| 4,013,582 | 3/1977 | Gavrilovic | 252/299 |
| 4,017,416 | 4/1977 | Ingkai et al. | 252/299 |
| 4,032,470 | 6/1977 | Bloom et al. | 252/299 |
| 4,035,056 | 7/1977 | Coates et al. | 252/299 |
| 4,006,708 | 9/1977 | DuBois | 252/299 |
| 4,077,260 | 3/1978 | Gray et al. | 252/299 |
| 4,082,428 | 4/1978 | Hsu | 252/299 |
| 4,083,797 | 4/1978 | Oh | 252/299 |
| 4,113,647 | 9/1978 | Coates et al. | 252/299 |

FOREIGN PATENT DOCUMENTS

| | | | |
|---|---|---|---|
| 2502904 | 7/1975 | Fed. Rep. of Germany | 252/299 |
| 2538865 | 3/1976 | Fed. Rep. of Germany | 252/299 |
| 2450088 | 4/1976 | Fed. Rep. of Germany | 252/299 |

OTHER PUBLICATIONS

Gray; G. W., et al., Mol Cryst. Liq. Cryst.. vol. 37, pp. 189–211, (1976).

Coates; D., et al., Mol. Cryst. Liq. Cryst., vol. 31, pp. 275–283, (1975).

Klanderman; B. H., et al., J. Am. Chem. Soc., vol. 97, No. 6, pp. 1585–1586, (1975).

Gray; G. W., et al., Electron Lett., vol. 9, No. 26, pp. 616–617, (1973).

Gray; G. W., et al., Electron Lett., vol. 11, No. 23, pp. 556–557, (1975).

*Primary Examiner*—Benjamin R. Padgett
*Assistant Examiner*—T. S. Gron
*Attorney, Agent, or Firm*—Stevens, Davis, Miller & Mosher

[57] ABSTRACT

The present invention discloses chiral thermochromic liquid crystal mixtures which do not contain cholesterol or sterol residues.

11 Claims, No Drawings

OPTICALLY ACTIVE LIQUID CRYSTAL MIXTURES AND LIQUID CRYSTAL DEVICES CONTAINING THEM

The present invention relates to optically active liquid crystal mixtures and liquid crystal devices containing them.

It is known to mix together compounds having liquid crystal properties or tendencies to produce mixtures with extended liquid crystal temperature ranges. If the resulting mixtures are optically active they may find use in electro-optical devices of the cholestericto-nematic phase change kind, or in applications where the colour of the mixture can change with temperature (thermochromic applications eg surface thermography, temperature detection) or with the presence of an impurity (applications to detect unwanted particles, liquids or vapours, eg atmospheric pollutants).

Copending United Kingdom Patent Application No. 36211/75 describes such mixtures formed by mixing 4'-alkyl-4-cyanobiphenyls with 4''-alkyl-4-cyano-p-terphenyls.

In accordance with the present invention an optically active thermochromic mixture having liquid crystal properties or tendencies is formed from at least two compounds selected from the groups having the following formulae:

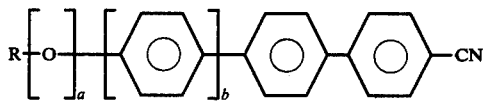
I wherein R is alkyl which may be straight chain, branched chain and may contain a chiral centre and includes up to 12 and preferably 10 carbon atoms, and a and b may have the values 0 or 1 such that $a+b = 0$ or 1;

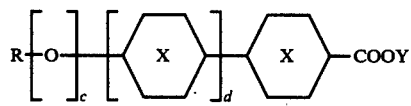
II where R is as defined for group I, $c = d = 0$ when

 represents 

and c and d may have the values 0, or 1 when

 represents 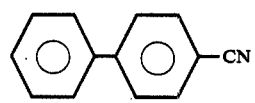

when $d = 0$, Y is selected from hydrogen,

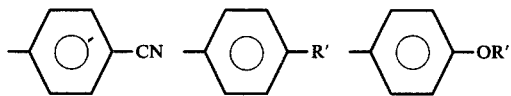

and when $d = 1$, Y is selected from hydrogen, $-R^1$,

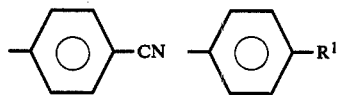

where $R^1$ is an alkyl group as defined for R in group I above;

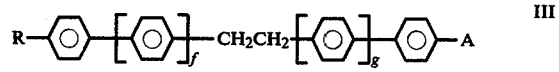
III where f and g may have the values 0, or 1 such that $f+g = 1$ and where A is $R^1$, $OR^1$ or CN where $R^1$ in an alkyl group as defined for R in Group I above;

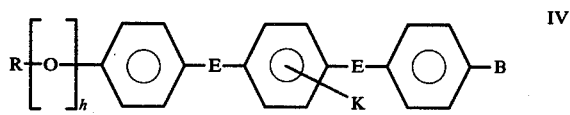
IV where h is 1 or 0, K is hydrogen or a lateral methyl or halogen (preferably chlorine) substituent, E is an ester linkage —OCO— or —COO—, and B is $R^1$, $OR^1$, or CN where $R^1$ is an alkyl group as defined for R in Group I; wherein at least one of the two said compounds has, as an alkyl end group R or $R^1$ a chiral alkyl group $AlkCH(Alk^1)(CH_2)_n$— where Alk and $Alk^1$ are different alkyl groups and n is an integer from 1 to 5 inclusive and wherein at least one of the said compounds is selected from Groups II, III and IV. Preferably the chiral alkyl group has the formula $CH_3CH_2CH(CH_3)(CH_2)_n$ where n is 1 to 3 inclusive above. If one of them is not chiral it may be normal or branched. The mixtures as defined above may be used in known applications for optically active liquid crystal materials, the actual application depending on the specific properties of the mixture, eg the helical pitch of its molecular arrangement. As is well understood in the liquid crystal art the thermochromic effect is dependent upon the pitch of the helical structure adopted by the liquid crystal material being of the order of the wavelength of visible light and also being temperature dependant. As is also well understood admixture of a non-chiral liquid crystal material with a chiral liquid crystal material the pitch tends to increase and accordingly the pitch of chiral liquid crystal material may be adjusted by admixture with non-chiral materials in appropriate proportions, which may be determined by trial and error. Preferably the mixtures are eutectics.

According to the invention in another aspect a liquid crystal electro-optic device or thermochromic device includes a mixture as defined above, and a method of determining the temperature of a surface includes the step of spreading a film of a mixture as defined above on a surface and observing the colour of the film at right angles to the surface by reflective light.

Compounds having the formulae set forth in Groups I and IV above are known and their methods of preparation are also known.

The optically active compounds produced as products in the following description have a positive optical rotation angle denoted by the symbol (+). Analogous compounds with negative optical rotation angles (−) or racemic compounds (±) may be prepared by analogous routes using the appropriate 'negative' or racemic reactants in the preparation routes.

Compounds having the formula II above and compounds used as intermediates in the production thereof.

EXAMPLE 1

The production of (+)-4-(2″-methylbutyl)biphenyl-4′- carboxylic acid by the following route:

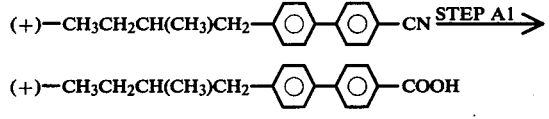

(+)-4-(2″-methylbutyl)-4′- cyanobiphenyl is known and its production is described in Copending United Kingdom Patent Application No. 36211/75 and elsewhere.

Step A1: The production of (+)-4-(2″-methylbutyl)biphenyl-4′-carboxylic acid.

One example of a way of carrying out this step is as follows:

(+)-4-(2″-Methylbutyl)-4′-cyanobiphenyl(0.01-5mole) is dissolved in methanol (50ml) and is added to a mixture of potassium hydroxide (0.54mole) and sodium hydroxide (0.75 mole) in methanol (40ml) and water (20ml). The solution is heated under reflux until evolution of ammonia ceases (approximately 72 hr). The mixture is diluted with water (1000ml) and acidified with concentrated hydrochoric acid. The precipitated product is filtered off and crystallised twice from ethanol. The product has a crystal - cholesteric liquid crystal transition temperature of 224° C; and a cholesteric liquid crystal - isotropic liquid transition temperature of 247° C.

EXAMPLE 2

The preparation of (+)-4-(3″-methylpentyl)biphenyl-4′-carboxylic acid by the following route:

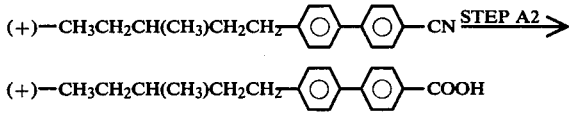

(+)-4-(3″-methylpentyl)-4′-cyanobiphenyl is a known compound and its preparation is described in Copending United Kingdom Patent Application No. 36211/75 and elsewhere.

Step A2: The production of (+)-4-(3″-methylpentyl)biphenyl-4′-carboxylic acid.

One example of a way of carrying out this step is as follows:

The acid is prepared and purified by a method analogous to that in step A1 of Example 1. The colourless crystals which are produced have a crystal - cholesteric liquid crystal transition temperature of 219° C; and a cholesteric liquid crystal - isotropic liquid transition temperature of 242° C.

EXAMPLE 3

The preparation of (+)-4-(4″-methylhexyl)biphenyl-4′-carboxylic acid by the following route:

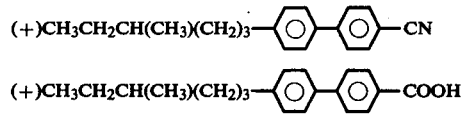

(+)-4-(4″-methylhexyl)-4′-cyanobiphenyl is known and its preparation is described in Copending United Kingdom Patent Application No. 36211/75.

Step A3: The production of (+)-4-(4″-methylhexyl)biphenyl-4′-carboxylic acid.

One example of a way of carrying out this step is as follows:

The acid is prepared and purified by a method analogous to that in step A1 of Example 1 and has the following physical properties C—$S_C$, 175.4° C; $S_C$—Ch, 219.1° C; Ch—I, 235.8° C.

EXAMPLE 4

The preparation of (+)-4-(2′-methybutyl)benzoic acid by the following route.

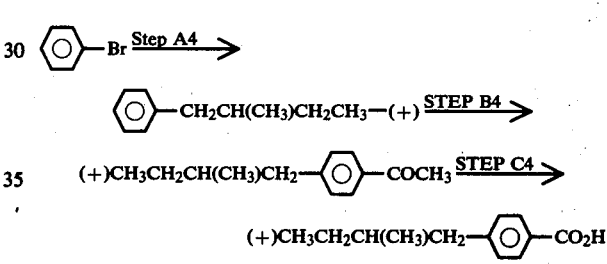

Step A4: The production of (+)-2methylbutylbenzene

One example of a way of carrying out this step is as follows:

A solution f bromobenzene (0.51 mole) in sodium dried ether (200ml) is added in drops to magnesium turnings (0.51 mole) in sodium dried ether (50ml). A single crystal of iodine is added to initiate the reaction. When addition is complete the solution is heated under reflux for 1 hour.

The Grignard reagent is then cooled in an ice bath and ferric chloride (0.0025 mole) in ether (2ml) is added. A solution of (+)-2-methylbutyl bromide (0.54 mole) (the preparation of which is known and described in United Kingdom Patent Application No. 36211/75) in sodium dried ether (100ml) is then added over 30 mins.

The reaction mixture is then left for 48 hours (woth stirring) at 25° C. After this time the mixture is poured into an ice-cold 20% hydrochloric acid solution and stirred for 30 mins. The product is extracted into ether and the combined extract is washed with water and dried ($Na_2SO_4$). The ether is evaporated off and the oily residue distilled. The fraction boiling at 120° C at 15 mm Hg pressure is collected.

Step B4: The production of (+)-4-(2-methylbutyl) acetophenone.

One example of a way of carrying out this step is as follows:

Crushed anhydrous aluminum trichloride (0.295 mole) is suspended in carbon disulphide (80ml). Acetyl chloride (0.25 mole) and 2-methylbutyl benzene, prepared in Step A4, are dissolved in carbon disulphide (80ml) and added to the aluminium trichloride suspension under anhydrous conditions; the mixture is left to stand overnight (with stirring).

The solvent is distilled from the reaction mixture and the viscous residue poured onto crushed ice and stirred for 30 min. The product is extracted into ether, washed with water and dried ($Na_2SO_4$). The ether is removed by rotary evaporation and the oily residue is distilled. The product boils at 95° C at a pressure of 0.1 mm Hg.

Step C4: The production of (+)-4-(2'-methybutyl) benzoic acid.

One example of a way of carrying out this step is as follows:

A solution of sodium hypo-bromite, prepared by dissolving bromine (156g) in a solution of sodium hydroxide (3.5 mole) in water (700ml) at 0° C, is added to a well stirred solution of (+)-4-(2'-methylbutyl) acetophenone (0.2 mole) prepared in step B4, in dioxan (500ml). Throughout the addition, and for 15 minutes after, the reaction temperature is maintained at 35–40° C.

Excess of hypobromite is destroyed by adding a solution of sodium metabisulphite. Water (3.5 liter) and bromoform are distilled from the reaction mixture.

On cooling, the solution is acidified with concentrated hydrochloric acid and the benzoic acid precipitated is filtered off and washed with water. The product is crystallised from ethanol/water. The melting point of the product is 130° C.

EXAMPLE 5

The preparation of (+)-4-(3'methylpentyl)benzoic acid by the following route:

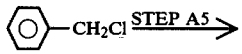

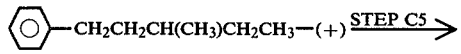

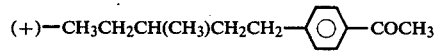

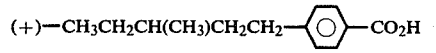

Step A5: The production of (+)-3methylpentylbenzene.

One example of a way of carrying out this step is as follows:

The Grignard reagent of commercially available benzyl chloride is prepared and alkylated in an analogous manner to step A4 of Example 4.

Step B5: The production of (+)-4-(3'-methylpentyl)acetophenone.

One example of a way of carrying out this Step is as follows:

The alkylbenzene prepared in Step A5 is acylated and purified in an analogous manner to Step B4 of Example 4.

Step C5: The production of (+)-4-(3'-methylpentyl)benzoic acid.

One example of a way of carrying out this step is as follows:

The acetophenone prepared in Step B5 is oxidised to the acid product (melting point 121°C.) by an analogous manner to Step C4 of Example 4.

EXAMPLE 6

The preparation of (+)-trans-4-alkylcyclohexane-1-carboxylic acids by the following route:

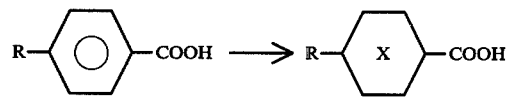

Step A6: The production of (+)-trans-4-alkylcyclohexane-1-carboxylic acids.

Ways of carrying out this step are exemplified by the preparation of (+)-trans-4-(2'-methylbutyl)cyclohexane-1-carboxylic acid as follows:

A solution of (+)-4-(2'-methylbutyl)benzoic acid (0.2 mole) in sodium hydroxide (6.205 mole) dissolved in water (160ml) is hydrogenated in the presence of Raney Nickel catalyst (10g) in an autoclave (1 liter) at 195° C. and a pressure of 170 atm of hydrogen for 30 hr.

On cooling, the catalyst is fltered off and the filtrate washed with ether. The aqueous layer is acidified and the precipitated acids are extracted into ether, washed with water and dried ($Na_2SO_4$). The ether is distilled off and the acids are taken up in methanol (200ml); the solution is treated successively with 40g and 30g of thiourea. After each treatment with thiourea, the crystallisate is filtered from the methanol. The combined crystallisates are dissolved in a 5% potassium hydroxide solution (800ml) which is then acidified and the (+)-trans-4-(2'-methylbutyl)cyclohexane-1-carboxylic acid precipitated is extracted into ether; the extract is washed with water and dried ($Na_2SO_4$).

The ether is evaporated off and the acid recrystallised from acetone. The melting point of the product is 50.3° C.

EXAMPLE 7

Preparation of 4'-cyano-4-hydroxybiphenyl by the following route:

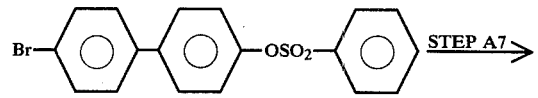

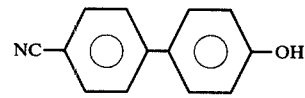

Step A7: The production of 4'-bromo-4-hydroxybiphenyl.

One example of a way of carrying out this Step is by a standard method using sodium hydroxide to hydrolyse commercially available 4'-bromo-4-benzenesulphonyloxybiphenyl in a mixture of water and dioxan as solvent. The colourless crystals obtained by crystallisation of the product from ethanol have a melting point of 166° C.

Step B7: The production of 4'-cyano-4-hydroxybiphenyl.

One example of a way of carrying out this step is as follows:

A mixture of 4'-bromo-4-hydroxybiphenyl (6g) N-methyl-2-pyrrolidone (23ml) and copper (I) cyanide (2.5g) is heated under reflux and vigorously stirred for 2 hr. The mixture is protected from atmospheric moisture using CaCl₂ guard tubes. After cooling, the mixture is poured into a warm (60°C.) solution of iron (III) chloride in water (200ml) and concentrated hydrochloric acid (8ml) and stirred (20 min). The cooled mixture is shaken twice with ether (2 × 100ml) and the combined organic extracts are water washed. Rotary evaporation of the solvent gives a pale brown solid which is crystallised from a mixture of water and ethanol. This yields pale tan needles of melting point 198° C.

EXAMPLE 8

The preparation of 4-alkylphenols - where the alkyl group may or may not be chiral.

These are prepared by standard methods such as those described by Van der Veen, de Jeu, Grobben and Boven (*Mol. Cryst. Liq. Cryst.*, 1972, 17, 291) for the preparation of 4-alkylanilines, followed by diazotisation of the amines and hydrolysis of the diazonium sulphates.

EXAMPLE 9

Preparation of 4-alkoxyphenols - where the alkyl chain may or may not be chiral.

These are prepared by the mono-alkylation of p-quinol using the method of Neubert, Carlino, D'Sidocky and Fishel (Liquid Crystals and Ordered Fluids', Vol. 2 (Edited by J F Johnson and R S Porter). Plenum Press, N.Y. 1973 p. 303). The colourless products are purified by column chromatography and crystallisation.

EXAMPLE 10

4-cyanophenol is a commercially available material.

EXAMPLE 11

Preparation of (+)-4-alkoxybenzoic acids.

One way of preparing these materials is by a standard method of alkylating hydroxy aromatic carboxylic acids (Gray and Brynmor Jones, *J Chem. Soc.*, 1954, 678), in this case 4-hydroxybenzoic acid.

EXAMPLE 12

Preparation of (+)-4-alkoxybiphenyl4'-carboxylic acids by the following route:

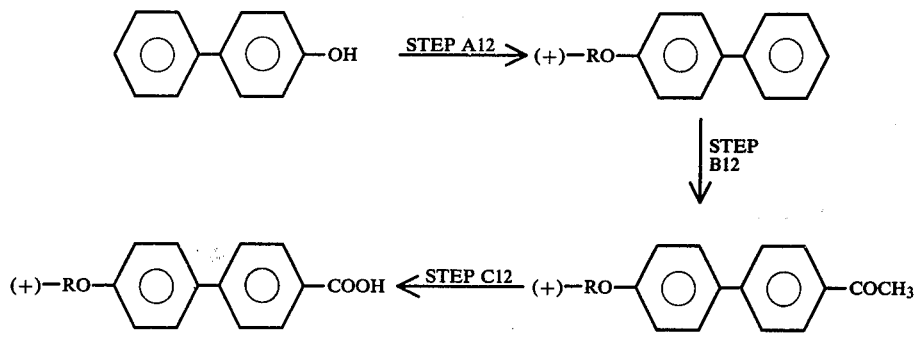

Step A12: The production of (+)-4-alkoxybiphenyl.

One example of a way of carrying out this Step is described by Coates and Gray, J. Chem. Soc., *Perkin II*, 1976, 863. Step B12: The production of (+)-4-alkoxy-4'-acetylbiphenyl.

One example of a way of carrying out this Step is by a Friedel-Crafts acylation as described in Step A15 of Example 15 below.

Step C12: The production of (+)-4-alkoxybiphenyl-4'-carboxylic acids.

One example of a way of carrying out this step is by a haloform oxidation reaction analogous to that described in step C4 of Example 4 above.

EXAMPLE 13

The preparation of ester compounds of Group II defined above by the following route:

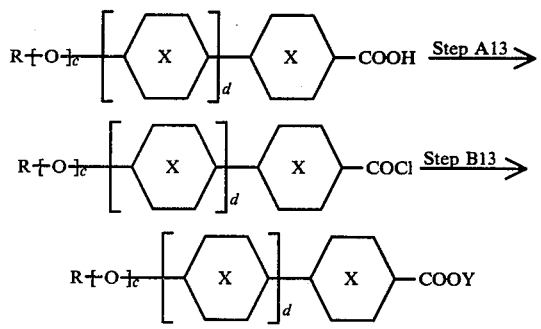

where R, c, d and Y are defined for Group II above save that Y is not hydrogen.

Step A13: The production of the optically active acid chloride.

The carrying out of this step is exemplified by the preparation of (+)-4-(2"-methylbutyl)biphenyl-4'-carboxylic acid chloride as follows: (+)-4-(2"-Methylbutyl)biphenyl-4'-carboxylic acid (0.002 mole) prepared in Step A1 of Example 1, is heated with thionyl chloride (20ml) under anhydrous conditions for 1.5 hr. The excess of thionyl chloride is removed by distillation under reduced pressure. The acid chloride residue is used in the next step without further purification.

Step B13: The production of the ester.

The carrying out of this step is exemplified by the production of 4''-n-pentylphenyl (+)-4-(2''-methylbutyl)biphenyl-4'-carboxylate.

(+)-4-(2''-Methylbutyl)biphenyl-4'-carboxylic acid chloride (0.002 mole), prepared in Step A13, is dissolved in dry 'AnalaR' (Trade Mark) pyridine (10Ml) and cooled in an ice bath. 4-n-Pentylphenol (0.002 mole), prepared as in Example 8, is added to the stirred solution and the mixture is left, with stirring, for 18 hr to rise to room temperature. It is then heated at 100° C. for 1 hr. The pyridine is removed by rotary evaporation and the residue column chromatographed on silica gel, eluting with chloroform. The combined fractions of ester are crystallised from hexane.

Analogous products prepared by Steps A13 and B13 involve the use of the analogous intermediate products produced by Examples 7, 8, 9 and 10.

The constants measured for some Examples of the esters of Group II are given in the Tables 1-8 below, in which the following symbols have the stated meaning: C = crystal; $S_A$ = Smectic A; Ch = cholesteric; I = isotropic liquid;→ = transition temperature; $\Delta H$ = enthalpy of fusion in k cal mol$^{-1}$ and the temperatures are in °C, for monotropic transitions, the temperatures are in parenthesis.

It should be noted that the chiral $S_C$ and Ch phases of any single compound always have the same sense (right or left-handed) of pitch. However, compounds having the value of n even in the grouping $CH_3CH_2CH(CH_3)(CH_2)_n$ — have right handed helical pitch senses whereas those with odd values of n have left-handed helical pitch senses for the $S_C$ and Ch phases.

TABLE 1

(+) —CH$_3$CH$_2$CH(CH$_3$)CH$_2$—⟨O⟩—⟨O⟩—COO—⟨O⟩—D

D = alkyl or cyano

| D | C → Ch(°C.) | Ch → I(°C.) | ΔH |
|---|---|---|---|
| —CN | 99.5 | 195.9 | 7.1 |
| —C$_2$H$_5$ | 81.3 | 141.1 | 5.7 |
| —C$_3$H$_7$ | 81.5 | 151.3 | 5.6 |
| —C$_4$H$_9$ | 65.6 | 127.5 | 4.4 |
| —C$_5$H$_{11}$ | 63.6 | 138.2 | 4.1 |
| —C$_6$H$_{13}$ | 60.3 | 132.3 | 6.5 |

TABLE 2

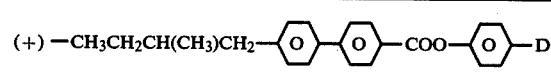

(+) —CH$_3$CH$_2$CH(CH$_3$)CH$_{2n}$—⟨O⟩—COO—⟨O⟩—⟨O⟩—CN

| n | C → ch °C. | Ch → I °C. | ΔH k cal mol$^{-1}$ |
|---|---|---|---|
| 1 | 96.5 | 210 | 5.2 |
| 2 | 99.2 | 205 | 4.5 |

TABLE 3

(+) —CH$_3$CH$_2$CH(CH$_3$)CH$_2$—⟨H⟩—COO—⟨O⟩—⟨O⟩—B

| B | C → $S_A$ °C. | $S_A$ → Ch °C. | Ch → I °C. | ΔH k cal mol$^{-1}$ |
|---|---|---|---|---|
| —CN | 77.6 | 138 | 190.4 | 4.63 |

TABLE 4

(+) —CH$_3$CH$_2$CH(CH$_3$)CH$_2$⟨H⟩—COO—⟨O⟩—OC$_n$H$_{2n+1}$

| n | C—I °C. | $S_A$—Ch °C. | Ch—I °C. | Pitch μm |
|---|---|---|---|---|
| 6 | 50.0 | — | (29.5) | 0.46 |
| 10 | 49.1 | (41.8) | (45.4) | 0.46 |

TABLE 5

(+) —CH$_3$CH$_2$CH(CH$_3$)CH$_2$⟨O⟩—COO—⟨O⟩—OC$_n$H$_{2n+1}$

| n | C—I °C. | Ch—I °C. | Pitch μm |
|---|---|---|---|
| 6 | 22 | (17) | 0.23 |
| 10 | 36 | (32) | 0.23 |

TABLE 6

(+) . CH$_3$CH$_2$CH(CH$_3$) . (CH$_2$)$_2$—⟨O⟩—CO .

O—⟨O⟩—OC$_n$H$_{2n+1}$

| n | C—Ch/I | Ch—I | Pitch μm |
|---|---|---|---|
| 7 | 27 | 27.4 | 0.32 |
| 8 | 32 | (30.4) | 0.32 |

TABLE 7

(+) . CH$_3$CH$_2$CH(CH$_3$)CH$_2$O—⟨O⟩—⟨O⟩—COO—⟨O⟩—A

| A | C—$S_C$ °C. | $S_B$—$S_C$ °C. | $S_C$—$S_A$ °C. | $S_A$—Ch °C. | CH—I °C. | Pitch μm |
|---|---|---|---|---|---|---|
| C$_6$H$_{13}$ | 72 | (67.8) | 85.5 | 145 | 158 | 1.2 |
| OC$_8$H$_{17}$ | 95 | — | 136.2 | 152.5 | 170 | 1.2 |

TABLE 8

(+) . CH$_3$CH$_2$CH(CH$_3$)(CH$_3$)$_3$—⟨O⟩—⟨O⟩—⟨O⟩—C$_7$H$_{15}$
                                              COO

C ——→$S_C$ ——→$S_A$ ——→Ch ——→I
91.5° C    93° C    112° C    131° C

Group III compounds

EXAMPLE 14

The production of (+)-1,2-[4'-{4''-(2'''-methylbutyl)-biphenylyl) - 4'''-cyanophenyl ethane by the following route:

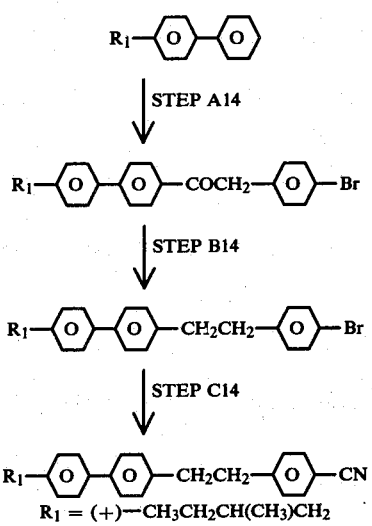

Step A14: The production of
(+)-4-[4'-(2'''-methylbutyl)biphenylyl]
4''-bromophenylmethyl ketone (by Friedel-Crafts Acylation).

One example of a way of carrying out this step is as follows:

A mixture (+)-2-methylbutylbiphenyl (0.08 mole) (the preparation of which is known and described in United Kingdom Patent Application No. 36211/75) 4-bromophenyl acetyl chloride (0.1 mole - prepared by standard methods from commercially available 4-bromophenyl acetic acid) and dry dichloromethane (140Ml) is added in drops to a mixture of dry dichloromethane (50Ml) and anhydrous aluminium trichloride (0.12 mole) cooled in an ice/salt bath to $-7°$ C. The mixture is stirred at between $-7°$ C. and $0°$ C. for 2 hr, and then at room temperature for 1 hr; it is then poured over ice, water and concentrated hydrochloric acid and the resultant mixture is stirred for 0.5 hr. The dichloromethane layer is separated, washed with water, dried, and evaporated to dryness; the residue is crystallised from ethanol/toluene. Its melting point is $154°$ C.

Step B14: The production of
(+)-1,2-[4'-(4''-{2'''''-methylbutyl}biphenylyl)
-4'''-bromophenyl]ethane.

One example of a way of carrying out this Step is as follows:

To lithium aluminium hydride (0.063 mole) in sodium - dried ether (100ml) are added:
(a) anhydrous aluminium trichloride (0.135 mole) in sodium - dried ether (100ml) and
(b) (+)-4-[4'-(2'''-methylbutyl)biphenylyl) 4''-bromophenylmethyl ketone (0.0185 mole) prepared in step A14, in dry chloroform (200ml) at such a rate that the mixture gently boils.

The reaction mixture is then left stirring and boiling for 18 hr. The excess of lithium aluminium hydride is then destroyed by cautiously adding water to the mixture.

The mixture is then poured into a solution of ice (200 g), water 60ml and concentrated hydrochloric acid (100ml) and left stirring for 0.5 hr.

The organic layer is separated off, washed with water (3 × 100ml), dried over anhydrous sodium sulphate and the ether is then evaporated off. The solid product is crystallised from ethanol/toluene; the melting point is $127°$ C.

Step C14; The production of
1,2-[4'-(2'''''-methylbutyl)biphenyl cyanophenyl} ethane.

One example of a way of carrying out this step is as follows:

The product from Step B14 (1g) is dissolved in dry, hot N-methyl-2-pyrrolidone (2ml); copper (I) cyanide (0.5g) is added and the mixture is vigorously stirred under reflux for 1.5 hr. On cooling, the mixture is poured into a solution of water (30ml), iron (III) chloride (3g) and concentrated hydrochloric acid (1ml) and stirred for 0.5 hr. at $60°$ C. After cooling, the mixture is shaken with chloroform; The chloroform layer is washed with water, dried over anhydrous sodium sulphate and evaporated to dryness. The residue is purified by column chromatgraphy on silicic acid using chloroform as eluent followed by crystallisation from ethanol. Constants for this product are given in Table 9 below.

EXAMPLE 15

The production of (+)-1,2-[4'-{4''-(-3''''-methylpentyl)biphenylyl)4'''-cyanobiphenyl) ethane by the following route:

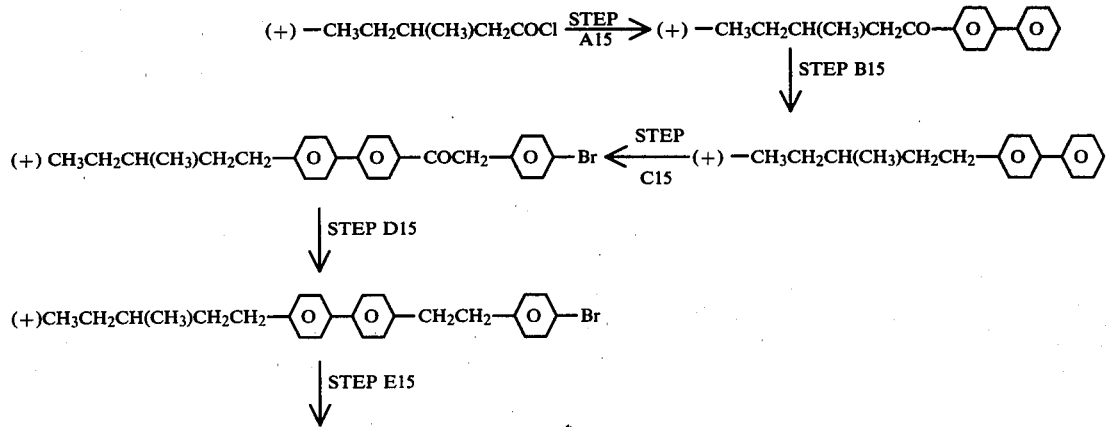

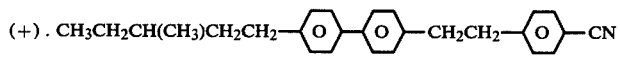
(+) . CH₃CH₂CH(CH₃)CH₂CH₂—⟨O⟩—⟨O⟩—CH₂CH₂—⟨O⟩—CN

Step A15: The production of (+)-4-(3'-methylpentanoyl)biphenyl

To commercially available biphenyl (0.08 mole) and anhydrous aluminium trichloride (0.1 mole) dissolved in dry nitrobenzene (90ml), (+)-3-methylpentanoylchloride (0.1mole) the preparation of which is known and described in United Kingdom Patent Application No. 36211/75), is added in drops, the temperature being maintained at about −7° C. during the addition. The mixture is then stirred for about 18 hr. with cooling in an ice bath. It is then poured onto a mixture of ice, water and concentrated hydrochloric acid and stirred for 0.5 hr., and the nitrobenzene layer is separated. The nitrobenzene is removed by steam distillation and the residue is crystallised from a small volume of ethanol to constant melting point.

Step B15: The production of (+)-4-(3'-methylpentyl)biphenyl by the following route:

One example of a way of carrying out this step is as follows:

The ketone produced in Step A 15 is reduced in a manner analogous to step B14 of Example 14. The product is purified by column chromatography and distillation.

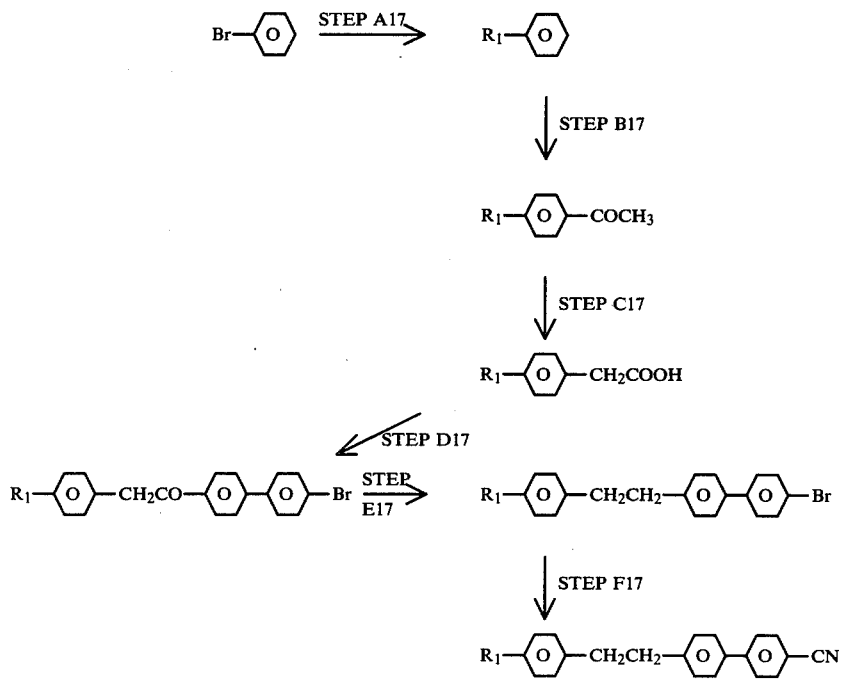

R₁ = CH₃CH₂CH(CH₃)CH₂

Step C15: The production of (+)-4-[4'-('''-methylpentyl)biphenylyl] 4''-bromophenylmethyl ketone (by Friedel-Crafts Acylation).

One example of a way of carrying out this step is a Step analogous to Step A14 of Example 14. The melting point of the product is 148.5° C.

Step D15: The production of (+-1,2-{4''-(3''''-methylpentyl}biphenylyl)4'''-bromophenyl] ethane.

One example of a way of carrying out this step is a step analogous to Step B14 of Example 14. The product is crystallised from ethanol and has a melting point of 136.3° C.

Step E15: The production of (+)-1,2-[4'-{4''-(3''''-methylpentyl)biphenylyl}-4'''-cyanophenyl] ethane:

One example of a way of carrying out this step is a step analogous to Step C14 of Example 14. Constants for the product are given in Table 9 below.

EXAMPLE 16

The production of (+)-1,2-[4'-{4''-(4''''-methylhexyl)-biphenylyl}-4'''-cyanophenyl] ethane.

This is prepared in an analogous manner to that described in Example 15, but starting with (+)-4-methylhexanoyl chloride, the preparation of which is known and described in United Kingdom Patent Application No. 36211/75.

EXAMPLE 17

The preparation of 1,2-[4'-2''''-methylbutyl phenyl-4''(4'''-cyanobiphenylyl] ethane by the following route Step A17, the production of (+)-2-methylbutybenzene, and Step B17 the production of 4-(+)-(2'-methylbutyl) acetophenone, may be carried out as described in Steps A4 and B4 of Example A respectively.

Step C17: The production of (+)-4-(2′-methylbutyl)phenylacetic acid.

One example of a way of carrying out this step is as follows:

A mixture of the acetophenone (0.2 mole), prepared in the previous step B17, sulphur (10.5g) and morpholine (65ml) is heated under reflux for 6 hr. The hot mixture is poured into methanol (250ml) and, after cooling, the solid is filtered off and washed with methanol.

The crude thioacetomorpholide (0.2 mole), 70% aqueous ethanol (380ml) and 50% aqueous sodium hydroxide solution (75ml) are refluxed for 8 hr. A volume of liquid equal to the ethanol present is removed by distillation and the residue is acidified with dilute hydrochloric acid. The crude acid is extracted into ether, the extract is dried (Na$_2$SO$_4$) and the ether evaporated off leaving the acid residue which is crystallised from ethanol/water.

Step D17: The production of (+)-4-(2″-methylbutyl)phenylacetyl-4′-bromobiphenyl (by Friedel-Crafts acylation).

This Step is carried out in a manner analogous to Step A14 of Example 14, the acid chloride being prepared from (+)4-(2′-methylbutyl)phenylacetic acid by a conventional method using thionyl chloride.

Step E17: The production of 1,2-[4′-(2″″-methylbutyl)phenyl-4″-(4‴-bromobiphenylyl)] ethane.

This Step is carried out in a manner, analogous to Step B14 of Example 14.

Step F17: The production of 1,2-[4′-(2″″-methylbutyl)phenyl-4″-(4‴-cyanobiphenylyl)] ethane.

This Step is carried out in a manner analogous to Step C14 of Example 14.

EXAMPLE 18

The preparation of 1,2-[4′-(3″″-methylpentyl)phenyl-4″-(4‴-cyanobiphenylyl)] ethane by the following route:

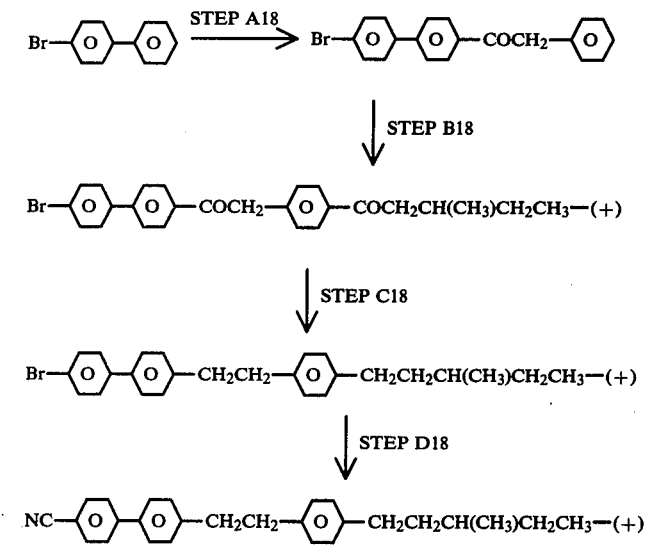

Steps A18 –D18: The production of 1,2[4′-(3″″-methylpentyl)phenyl-4″-(4‴-cyanobiphenylyl)) ethane.

This preparative route is known and is carried out in the manner described in United Kingdom Patent Application No. 16643/75 using (+)-3-methylpentanoyl chloride, the preparation of which is described in United Kingdom Patent Specification No. 1,433,130 as a starting material.

EXAMPLE 19

The preparation of 1,2[4′-(4″″-methylhexyl)phenyl-4″-(4‴-cyanobiphenylyl)] ethane.

This compound is prepared by a route analogous to that in Example 18, but using (+)-4-methylhexanoylchloride, as a starting material.

EXAMPLE 20

Preparation of (+)-1, 2-[4′-alkoxyphenyl-4″-(4‴-cyanobiphenylyl)] ethanes by the following route:

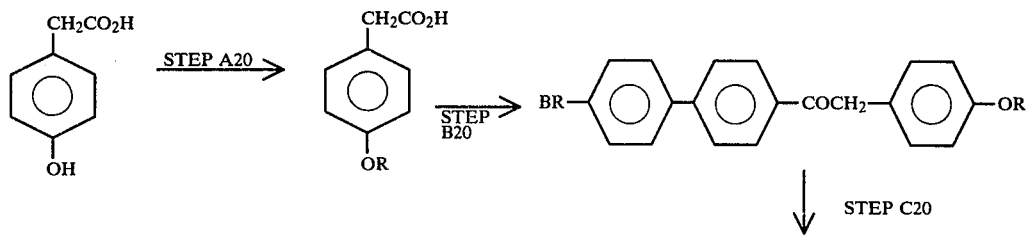

Step A20: The production of (+)-4-alkoxyphenylacetic acids.

One example of a way of carrying out this Step is as follows:

This alkylation is carried out by standard techniques starting with commercially available 4-hydroxyphenylacetic acid which is heated with the chiral alkyl bromide and sodium hyrdoxide in aqueous ethanol -(see, Gray and Jones, *J Chem. Soc.*, 1954, 678).

Step B20: The production of (+)-4-alkoxyphenylmethyl 4″-(4‴-bromobiphenylyl) ketones (by Friedel-Crafts Acylation).

This Step is carried out in a manner similar to Step A14, but the reaction mixture is heated for 4 hr under reflux (instead of being cooled in ice for 2 hr). The acid chloride used in the reaction is prepared from the product of Step A20 by a conventional method using thionyl chloride.

Steps C20 and D20: These steps are achieved by methods analogous to Steps B14 and C14, respectively.

EXAMPLE 21 ;1

The preparation of (+)1,2-[4′-(4″-alkyl/alkoxy-biphenylyl)-4‴-alkyl/alkoxy-phenyl] ethanes.

These compounds whose formulae are given in List 1 below are prepared by the Friedel-Crafts acylation reactions described in above Examples using either 4-alkyl or 4-alkoxyphenylacetyl chlorides and reacting them with either 4-alkylbiphenyls. The ketones are reduced to give the desired products in the same way as described in above Examples.

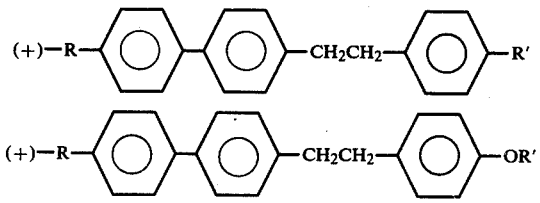

Where R is an alkyl group and R′ is an alkyl group which may be the same or different and at least one of the alkyl groups is chiral.

Physical constants for Examples of the compounds of Group III are given in the following table, the compounds being of the form

TABLE 9

(+)-CH₃CH₂CH(CH₃)(CH₂)ₙ—⟨O⟩—⟨O⟩—CH₂CH₂—⟨O⟩—CN

| n | C→Ch °C. | Ch→I °C. | Pitch (μm) 10% in 5CB | $[\alpha]_D^{20}$ |
|---|----------|----------|----------------------|---------|
| 1 | 91.7 | 103.4 | 1.5 | 7.6 |
| 2 | 91.6 | 110.8 | 4.5 | 9.6 |
| 3 | 95.0 | 105.8 | 4.3 | — |

Key to Tables 1 to 9

→S or Ch or I is the crystal to smetic, cholesteric, or isotropic liquid transition $S_1 - S_2$ is a smectic to smectic transition, where different smectic types are designated $S_A$, $S_B$, $S_C$.

$S_1$ - Ch is the smetic to cholesteric transition

ΔH is the total enthalpy of fusion for the change from stable crystal (C) to $S_A$ or Ch liquid crystal phase.

$[\alpha]_D^{20}$ is an absolute measure of the rotatory power (specific rotation) of an optically active material when forming a 10% w/v solution in chloroform.

Pitch is the molecular helical pitch of the compound (10%) when forming a mixture with 90% of 4-n-pentyl-4′-cyanobiphenyl (hereafter designated 5CB).

The following are examples of mixtures which exhibit cholesteric liquid crystal phases at or near room temperature. The mixtures incorporate compounds of Groups II and III defined above and also members of the series of chiral 4-alkyl-4′-cyanobiphenyls (Group I).

Mixture I

20% by weight

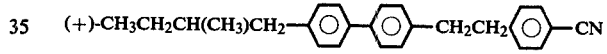

and

80% by weight

This mixture has a Smectic A-to-cholesteric transition at -3° C and a cholesteric-to-isotropic liquid transition at 15° C.

Mixture I is thermochromic and the selective colour reflected by the mixture when in the Grandjean plane texture as follows:

| Selective Reflection | Temperature (°C.) |
|----------------------|-------------------|
| Red | −3.0 |
| Yellow | −2.5 |
| Green | −2.0 |
| Turquoise | −1.5 |
| Blue | −1.0 |

Mixture II

20% by weight

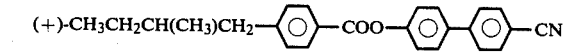

and

80% by weight

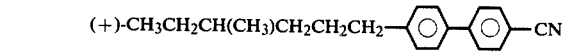

This mixture has a smectic A to cholesteric transition at −10° C. and a cholesteric to isotropic liquid transition at +19° C.

Mixture 2 is thermochromic giving the following selective colour reflections (in the Grandjean plane texture).

| Selective Reflection | Temperature (°C.) |
|---|---|
| Red | −10.0 |
| Green | −9.0 |
| Turquoise | −8.0 |
| Blue | −7.0 |

Mixture III

12% by weight

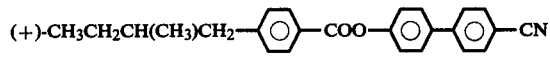

8% by weight

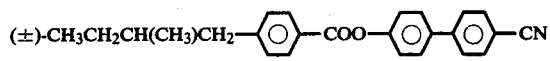

80% by weight

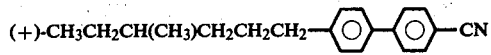

This mixture has a Smectic A to cholesteric transition at −10° C. and a cholesteric to isotropic liquid transition at +19° C.

Mixture III is thermochromic and the selective colour reflected by this mixture in the Grandjean plane texture is as follows:

| Selective Reflection | Temperature (°C.) |
|---|---|
| Red | −10.0 |
| Orange | −9.5 |
| Yellow | −8.5 |
| Green | −7.0 |
| Turquoise | −3.0 |
| Blue | +16.0 |

Mixture III demonstrates the use of racemic materials (±) in widening colour ranges in respect of temperature.

Mixture IV 42.5% by weight

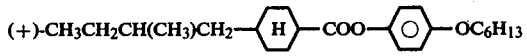

28.0% by weight

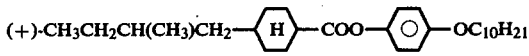

29.5% by weight

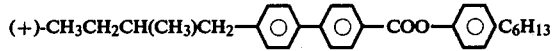

$S_C$ - Ch; 20° C Ch - I 57.4° C.

| Selective Reflection | Temperature (°C.) |
|---|---|
| Infra-red | 20 |
| Red | 28 |
| Yellow | 34 |
| Green | 36 |
| Turquoise | 45 |
| Blue | 47 |
| Isotropic liquid | 57.4 |

Mixture V 37.5% by weight

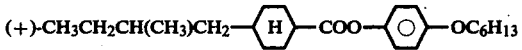

62.5% by weight

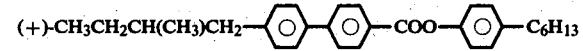

$S_C$-Ch, 27° C; Ch-I, 86° C.

| Selective Reflection | Temperature (°C.) |
|---|---|
| Red | 27.0 |
| Yellow | 29.5 |
| Green | 31.0 |
| Turquoise | 37.0 |
| Blue | 39.0 |
| Isotropic | 86.0 |

Mixture VI

14% by weight 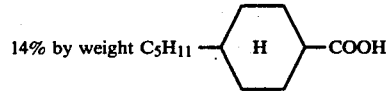

17% by weight 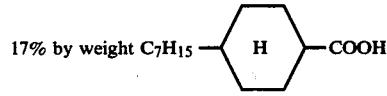

63% by weight 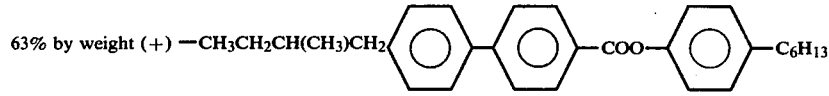

6% by weight 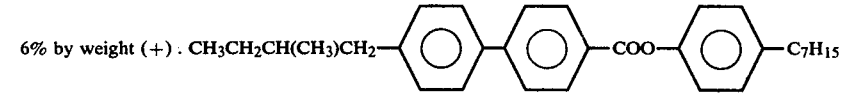

$S_A$-Ch, 22° C; Ch-I, 107.8° C.

| Selective Reflection | Temperature (°C.) |
|---|---|
| Red | 27 |

-continued

| Selective Reflection | Temperature (°C.) |
| --- | --- |
| Yellow | 45 |
| Green | 54 |
| Turquoise | 97 |
| Blue | 105 |
| Isotropic | 107.8 |

Examples of the use of mixtures as hereinbefore defined, eg in electro-optic phase change devices (when mixed with nematic materials) and in thermochromic devices, are described in copending United Kingdom Patent Application No 36211/75.

What we claim is:

1. A liquid crystal composition which comprises at least two optically active compounds selected from the group consisting of compounds having the general formulae

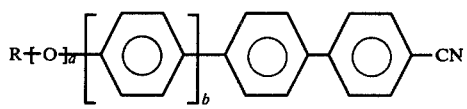
(1)

where R is a branched alkyl chain group which contains a chiral center and includes up to 12 carbon atoms, and a and b are 0 to 1 and a+b = 0 or 1:

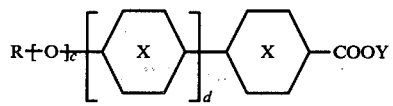
(2)

where R is alkyl, which may be straight chain, branched chain and may or may not contain a chiral center and includes up to 12 carbon atoms, c = d = 0 when

and c and d may be 0 or 1 when

when d = , Y is selected from hydrogen,

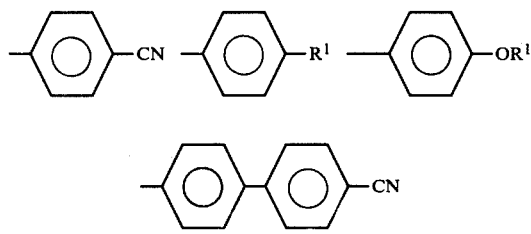

and when d = 1, Y is selected from hydrogen, $R^1$,

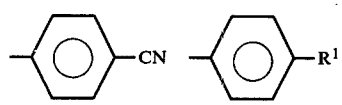

where $R^1$ an alkyl group as defined for R in group member (2);

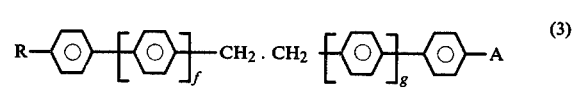
(3)

where R is defined as for group member (2), f and g may have values 0, or 1 such that f+g = 1 and where A is $R^1$, $OR^1$ or CN where $R^1$ is an alkyl group as defined for R in group member (2); and

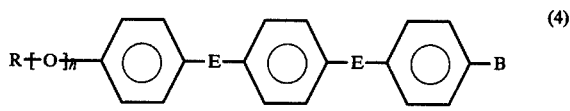
(4)

where R is defined as for group member 2, h is 1 or 0, E is an ester linkage —OCO— or —COO—, and B is $R^1$, $OR^1$, or CN where $R^1$ is an alkyl group as defined for R in group member (2); wherein each of the at least two said optically active compounds has as an alkyl end group R or $R^1$ a chiral alkyl group $AlkCH(Alk^1)(CH_2)_n$— where Alk and $Alk^1$ are different alkyl groups and n is an integer from 1 to 5 inclusive, and wherein at least one of the at least two said optically active compounds is selected from group members (2), (3) and (4), and wherein all of the optically active compounds in the composition have the same optical rotation angle sense and the liquid crystal composition has a helical structure having a pitch of the order of the wavelength of visible light and which composition is temperature dependent such that the composition is thermochromic.

2. A liquid crystal composition as claimed in claim 1 and wherein the chiral alkyl group as the formula $CH_3CH_2CH(CH_3)(CH_2)_n$— where n has the value one to three inclusive.

3. A liquid crystal composition as claimed in claim 1 and wherein the at least two said optically active compounds are selected from group member (2).

4. A liquid crystal composition as claimed in claim 1 and wherein,
(i) the group (1) compounds are selected from 4-alkyl-, and 4-alkyloxycyanobiphenyls and 4-alkyl-cyanoterphenyls in which the alkyl group containing a chiral center has up to 10 carbon atoms;
(ii) the group (2) compounds are selected from the group consisting of compounds having the general formula

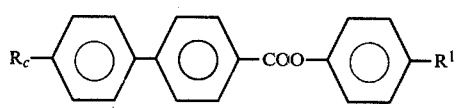

where $R_c$ is (+)—$CH_3CH_2CH(CH_3)CH_2$— and $R^1$ is a cyano group or an alkyl group containing up to six carbon atoms, 5. A liquid crystal composition as claimed in claim 1 and having the composition,

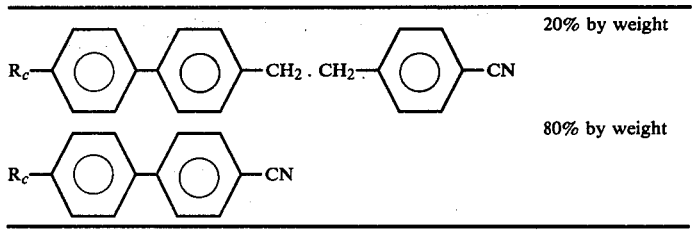

| | |
|---|---|
| (top structure) | 20% by weight |
| (bottom structure) | 80% by weight | where $R_c$ is (+)—$CH_3CH_2CH(CH_3)CH_2$—, and having a cholesteric thermochromic range from $-3°$ C. to $+15°$ C. and demonstrating the following selective reflections:
- red: $-3.0°$ C.
- yellow: $-2.5°$ C.
- green: $-2.0°$ C.
- turquoise: $-1.5°$ C.
- blue $-1.0°$ C.

6. A liquid crystal composition as claimed in claim 1 and having the composition

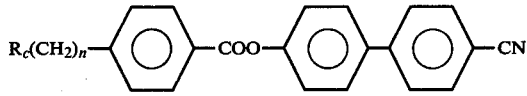

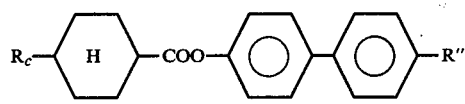

where n is one or two,

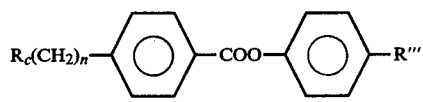

where R" is a cyano group or an alkyloxy group containing up to ten carbon atoms,

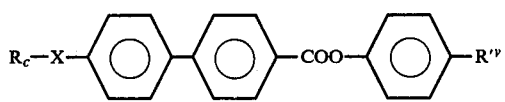

where n is one or two and R''' is an alkyl group containing up to ten carbon atoms, and

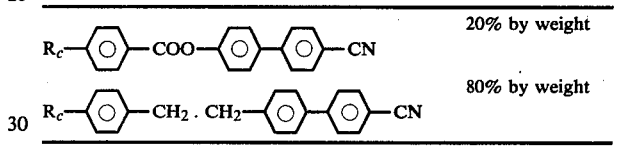

where X is —O—, —$(CH_2)_3$— and $R'^v$ is an alkyl or alkyloxy group containing up to eight carbon atoms,

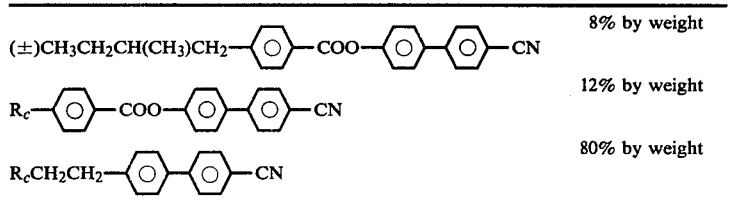

| | |
|---|---|
| (top structure) | 20% by weight |
| (bottom structure) | 80% by weight | where $R_c$ is (+)—$CH_3CH_2CH(CH_3)CH_2$—, and having a cholesteric thermochromic range from $-10°$ C. to $+19°$ C. and demonstrating the following selective reflections:
- red $-10°$ C.
- green $-9.0°$ C.
- turquoise $-8.0°$ C.
- blue $-7.0°$ C.

7. A liquid crystal composition as claimed in claim 1 and having the composition

| | |
|---|---|
| (first structure) | 8% by weight |
| (second structure) | 12% by weight |
| (third structure) | 80% by weight | and
(iii) the group (3) compounds are selected from compounds having the general formula

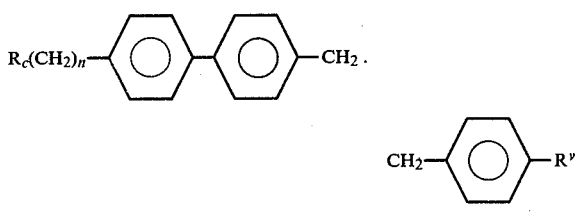

where n is zero, one, or two and $R^v$ is a cyano group or an alkyl or alkyloxy group containing up to ten carbon atoms.

where $R_c$ is (+)—$CH_3CH_2CH(CH_3)CH_2$—, and having a cholesteric thermochromic range from $-10°$ C. to $+19°$ C. and demonstrating the following selective reflections:
- red $-10.0°$ C.
- orange $-9.5°$ C.
- yellow $-8.5°$ C.
- green $-7.0°$ C.
- turquoise $-3.0°$ C.
- blue $+16.0°$ C.

8. A liquid crystal composition as claimed in claim 1 and having the composition

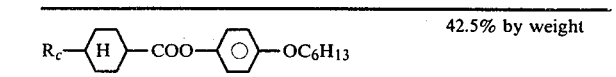

42.5% by weight

-continued

| | |
|---|---|
| $R_c\text{—}\langle H \rangle\text{—COO—}\langle O \rangle\text{—OC}_{10}H_{21}$ | 28.0% by weight |
| $R_c\text{—}\langle O \rangle\text{—}\langle O \rangle\text{—COO—}\langle O \rangle\text{—C}_6H_{13}$ | 29.5% by weight | where $R_c$ is $(+)$—$CH_3CH_2CH(CH_3)CH_2$—, and having a cholesteric thermochromic range from 20° C. to 57.4° C. and demonstrating the following selective reflections:
  red 28° C.
  yellow 34° C.
  green 36° C.
  turquoise 45° C.
  blue 47° C.

9. A liquid crystal composition as claimed in claim 1 and having the composition

| | |
|---|---|
| $R_c\text{—}\langle O \rangle\text{—COO—}\langle O \rangle\text{—OC}_6H_{13}$ | 37.5% by weight |
| $R_c\text{—}\langle O \rangle\text{—}\langle O \rangle\text{—COO—}\langle O \rangle\text{—C}_6H_{13}$ | 62.5% by weight | where $R_c$ is $(+)$—$CH_3CH_2CH(CH_3)CH_2$—, and having a cholesteric thermochromic range from 27° C to 86° C. and demonstrating the following selective reflections:
  red 27.0° C.
  yellow 29.5° C.
  green 31.0° C.
  turquoise 32.0° C.
  blue 39.0° C.

10. A liquid crystal composition as claimed in claim 1 and having the composition

| | |
|---|---|
| $C_5H_{11}\text{—}\langle H \rangle\text{—COOH}$ | 14% by weight |
| $C_7H_{15}\text{—}\langle H \rangle\text{—COOH}$ | 17% by weight |
| $R_c\text{—}\langle O \rangle\text{—}\langle O \rangle\text{—COO—}\langle O \rangle\text{—C}_6H_{13}$ | 63% by weight |
| $R_c\text{—}\langle O \rangle\text{—}\langle O \rangle\text{—COO—}\langle O \rangle\text{—C}_7H_{15}$ | 6% by weight | where $R_c$ is $(+)$—$CH_3CH_2CH(CH_3)CH_2$—, and having a cholesteric thermochromic range from 22° C. to 107.8° C. and demonstrating the following selective reflections
  red 27° C.
  yellow 45° C.
  green 54° C.
  turquoise 97° C.
  blue 105° C.

11. A method of determining the temperature of a surface which includes the step of spreading a film comprising a liquid crystal composition as claimed in claim 1 on the said surface and observing the color of the film at right angles to the surface by reflective light.

* * * * *